US005922560A

United States Patent [19]
Jacobson et al.

[11] Patent Number: 5,922,560
[45] Date of Patent: Jul. 13, 1999

[54] **ASTAXANTHIN OVER-PRODUCING STRAINS OF *PHAFFIA RHODOZYMA*, METHODS FOR THEIR CULTIVATION, AND THEIR USE IN ANIMAL FEEDS**

[75] Inventors: Gunnard Kenneth Jacobson, Brown Deer; Setsuko Omata Jolly, Glendale; Joseph James Sedmak, Brookfield; Thomas Joseph Skatrud, Menomonee Falls; John Marion Wasileski, Brown Deer, all of Wis.

[73] Assignee: Archer Daniels Midland Company, Decatur, Ill.

[21] Appl. No.: 08/557,714

[22] Filed: Nov. 13, 1995

Related U.S. Application Data

[63] Continuation of application No. 08/049,825, Apr. 19, 1993, Pat. No. 5,466,599.

[51] Int. Cl.$^6$ ............................ C12P 23/00; C12N 1/16
[52] U.S. Cl. ........................................ 435/67; 435/255.1
[58] Field of Search ................................. 435/67, 255.1

[56] References Cited

U.S. PATENT DOCUMENTS

| | | | |
|---|---|---|---|
| 5,182,208 | 1/1993 | Johnson et al. | 435/254 |
| 5,356,809 | 10/1994 | Johnson et al. | 435/225.1 |
| 5,356,810 | 10/1994 | Fleno et al. | 435/255.1 |
| 5,599,711 | 2/1997 | Fleno et al. | 435/255.1 |

FOREIGN PATENT DOCUMENTS

| | | | |
|---|---|---|---|
| 0 427 405 A1 | 5/1991 | European Pat. Off. | C12P 23/00 |
| 0 438 182 A1 | 7/1991 | European Pat. Off. | C12P 23/00 |
| 438182 | 7/1991 | European Pat. Off. | . |
| 0 454 024 A2 | 10/1991 | European Pat. Off. | C12P 23/00 |
| 0 474 347 A1 | 3/1992 | European Pat. Off. | C12P 23/00 |
| 57-206342 | 12/1982 | Japan | A23K 1/18 |
| 2238855 | 9/1990 | Japan | . |
| 90JP-285090 | 1/1992 | Japan | A23K 1/16 |
| WO 88/08025 | 10/1988 | WIPO | C12N 1/16 |
| WO 90/01552 | 2/1990 | WIPO | C12P 1/02 |
| WO 91/02060 | 2/1991 | WIPO | C12N 15/01 |
| WO 92/22648 | 12/1992 | WIPO | C12N 15/01 |

OTHER PUBLICATIONS

Johnson, E.A., "Astaxanthin Production by the Yeast *Phaffia rhodozyma* and Its Use as a Pigment Source in Animal Feeding," Master's Thesis, University of California, Davis (1978).

Johnson, E.A. et al., "Simple Method for the Isolation of Astaxanthin from the Basidiomycetous Yeast *Phaffia rhodozyma*," *Appl. Environ. Microbiol.* 35(6):1155–1159 (1978).

Johnson, E.A. and Lewis, M.J., "Astaxanthin Formation by the Yeast *Phaffia rhodozyma*," *J. Gen. Microbiol.* 115:173–183 (1979).

Declaration of Arnold Lester Demain, From Appeal Case No. T737/96–334 filed against the Decision of the Opposition Division dated Jun. 27, 1996.

Declaration of Gary W. Sanderson, From Appeal Case No. T737/96–334 filed against the Decision of the Opposition Division dated Jun. 27, 1996.

Statement of Grounds of Appeal on Behalf of Universal Foods Corporation, From Appeal Case No. T737/96–334 filed against the Decision of the Opposition Division dated Jun. 27, 1996.

Interlocutory Decision in Opposition Proceedings (Article 106(3), EPC), Issued in European Application No. 88903778.4–2105, Jun. 27, 1996.

Igene Biotechnology, Inc.'s Opposition to Archer Daniels Midland's Motion for Preliminary Injunction from Civil Action No. S97–2358 (Aug. 12, 1997).

Declaration of Robert Todd Lorenz from Civil Action No. S97–2358 (Aug. 11, 1997).

Affidavit of Ramin Abrishamian from Civil Action No. S97–2358 (Aug. 8, 1997).

Declaration of Patrick Monahan from Civil Action No. S97–2358 (Aug. 11, 1997).

Declaration of John Louis Harris from Civil Action No. S97–2358 (Aug. 11, 1997).

Declaration of Stephen Hiu with Attached Exhibits SH1–SH17 from Civil Action No. S97–2358 (Aug. 11, 1997).

Igene Biotechnology, Inc.'s Answer to Archer Daniels Midland Corp. Complaint and Counterclaims from Civil Action No. S97–2358 (Aug. 25, 1997).

Declaration No. 4 of Thomas J. Skatrud, Ph.D. from Civil Action No. S97–2358 (Aug. 27, 1997).

Declaration No. 1 of Gunnard K. Jacobson, Ph.D. with Attached Exhibits 1–3 from Civil Action No. S97–2358 (Aug. 27, 1997).

Archer Daniels Midland Corp.'s Reply to Igene Biotechnology Inc.'s Opposition to Archer Daniel Midland Corp.'s Motion for Preliminary Injunction with Attached Exhibits 1–5 from Civil Action No. S97–2358 (Aug. 29, 1997).

(List continued on next page.)

*Primary Examiner*—Herbert J. Lilling
*Attorney, Agent, or Firm*—Sterne, Kessler, Goldstein & Fox P.L.L.C.

[57] ABSTRACT

*Phaffia rhodozyma* strains are described which produce greater than 3,000 ppm astaxanthin based on dry yeast solids when cultivated in a volume of nutrient medium of at least about 1,500 liters and containing in excess of 4 percent, preferably in excess of 6 percent, dry yeast solids. These and other strains are cultivated by an improved fermentation method comprising extending the maturation phase of the fermentation by one or more various techniques including exposing the yeast cells to a low-intensity light, slow feeding the cells with a rapidly metabolized energy source e.g. glucose, and replacing the rapidly metabolized energy source with a slowly metabolized energy source, e.g. gylcerol. The cells of these strains are incorporated into animal feeds, particularly feeds for salmonid fishes, to impart or enhance the red pigmentation of these animals and products made from these animals.

7 Claims, 5 Drawing Sheets

OTHER PUBLICATIONS

Torrissen, 1989. Proc. Third Int. Symp. on Feeding and Nutr. in Fish, Toba Aug. 28–Sep. 1, Japan, pp. 387–399.

Meyers and Chen, 1982. Word Aquaculture Society, Special Publication No. 3, pp. 153–165.

Miller, Yoneyama and Soneda. 1976. Int. J. Syst. Bacteriol. 26:286–291.

Andrewes, Phaff and Starr. 1976. Phytochem. 15:1003–1007.

Johnson, Conklin and Lewis. 1977. J. Fish. Res. Board. Can. 34:2417–2421.

Johnson, Villa and Lewis. 1980. Aquaculture. 20:123–134).

Torrissen, Hardy and Shearer, 1989. CRC Crit. Rev. Aquatic Sci. 1:209–225.

Johnson and An. 1991. CRC Crit. Rev. Biotech. 11:297–326.

Official Method of Analysis, A.O.A.C. 14th Edition (1984) Sections 10.215–10.225.

An and Johnson Antonie van Leeuwenhoek. 1991. 57: 191–203.

Sedmak, Weerasinghe and Jolly. 1990. *Biotechnology Techniques,* vol. 4, No. 2, pp. 107–112.

Binkowski, Sedmak and Jolly. 1993. Aquaculture Magazine Mar./Apr. pp. 1–4.

Gentles and Haard. 1991. The Progressive Fish–Culturist 53: 1–6.

UBV-AX1
500x

UBV-AX1
1250x

UBV-AX2
500 x

UBV-AX2
1250 x

UBV-AX3
500 x

UBV-AX3
1250 x

UBV-AX4
500 x

UBV-AX4
1250 x

ASTAXANTHIN OVER-PRODUCING STRAINS OF *PHAFFIA RHODOZYMA*, METHODS FOR THEIR CULTIVATION, AND THEIR USE IN ANIMAL FEEDS

This is a continuation of application Ser. No. 08/049,825 filed on Apr. 19, 1993 now U.S. Pat. No. 5,466,599.

BACKGROUND OF THE INVENTION

This invention relates to astaxanthin. In one aspect, the invention relates to astaxanthin produced by yeast cells while in another aspect, the invention relates to methods of producing and cultivating mutant strains of *Phaffia rhodozyma* yeast cells that produce astaxanthin in excess of the typical *Phaffia rhodozyma* yeast cell found in nature. In yet another aspect, the invention relates to using products made from these yeast cells as a dietary supplement in various animal feeds.

A distinct red color is of prime importance to customer acceptance of certain food products, particularly aquatic food animals such as salmon, sea bream, trout, shrimp, lobster and many other marine animals. The oxygenated carotenoid astaxanthin (3,3'-dihydroxy-$\beta,\beta$-carotene-4,4,'-dione) is responsible for the red color of these aquatic animals. In addition to being responsible for the characteristic color of these animals, astaxanthin plays a critical nutritional role in the life of these marine animals (Torrissen, 1989. Proc. Third Int. Symp. on Feeding and Nutr. in Fish, Toba August 28–September 1, Japan, pp. 387–399, Meyers and Chen, 1982. World Aquaculture Society, Special Publication No. 3, pp. 153–165). These references are incorporated herein by references. This carotenoid is also useful for adding pigmentation to the flesh and products of other animals, and to other foodstuffs, e.g. poultry and eggs, various dairy products, snack foods, and the like.

Astaxanthin is the most abundant carotenoid present in the aquatic world. Aquatic animals, like terrestrial animals, generally cannot synthesize astaxanthin or any other carotenoid, although many of these animals accumulate caroteniod compounds that are present in their diets. Some of these animals, such as crustaceans, can interconvert some carotenes to oxygenated forms of carotenoids (called xanthophylls) of which astaxanthin is the predominant compound formed. However, salmonid fishes and red sea bream accumulate dietary astaxanthin even though these fish cannot convert any other carotenoid compound to astaxanthin. Therefore, the astaxanthin present in salmonid and sea bream fish, and in products produced from these fish, must be derived directly from dietary sources.

Plants, including marine microalgae and special yeasts such as *Phaffia rhodozyma*, are the primary source of carotenoid compounds in the world. As noted above, carotenoids are not biosynthesized de novo by animals. However, animals in general require certain carotenoids from which they benefit directly or indirectly, and these carotenoids are obtained from dietary sources. Examples of substances essential to most animals that are derived from certain carotenoids are vitamin A and rhodopsin. In the marine world, animals that are low on the food chain, such as crustaceans, eat microalgae and other carotenoid containing organisms from the plant world, and convert the carotenoid compounds present in large part to astaxanthin by natural metabolic processes. The astaxanthin is then stored in the body of these astaxanthin producing animals.

Wild grown salmonid fishes and red sea bream obtain their astaxanthin from the crustaceans and other astaxanthin containing organisms that make up an important part of their diet. In the case of pen-grown salmonids and red sea bream, the feeds used to produce these fish must be supplemented with astaxanthin in order to provide a dietary source of this important natural constitutent of these fishes. Currently, synthetic astaxanthin is added to feeds prepared for production of salmonids and red sea bream in aquaculture to provide a source of this carotenoid compound. In some cases, synthetic canthaxanthin (an oxygenated carotenoid compound that is very closely related to astaxanthin) is used in place of astaxanthin in feeds for salmonids and red sea bream, but this compound does not function as well in these fishes as the naturally predominant astaxanthin.

Natural sources of dietary astaxanthin are in great demand by the aquacultural industries. Natural sources of dietary carotenoids that have been investigated for farmed fish include krill, crawfish, crustacean processing by-products, algae and higher plants. However, these natural sources tend to be too expensive and of limited availability and reliability to be commercially viable.

The red yeast, *Phaffia rhodozyma*, has received great attention from industry as a natural source of astaxanthin since it was isolated from tree sap, and the red color identified as astaxanthin (Miller, Yoneyama and Soneda. 1976. Int. J. Syst. Bacteriol. 26:286–291, Andrewes, Phaff and Starr. 1976. Phytochem. 15:1003–1007) *Phaffia rhodozyma* was first demonstrated to pigment salmonid fishes in 1977 (Johnson, Conklin and Lewis. 1977. J. Fish. Res. Board. Can. 34:2417–2421, Johnson, Villa and Lewis. 1980. Aquaculture. 20:123–134). The potential advantages of *Phaffia rhodozyma* as a source of carotenoid pigments for aquaculture are that it is a natural product rich in essential nutrients (e.g. protein, lipids and B-vitamins) and that it contains astaxanthin (Johnson, Villa and Lewis. 1980. Aquaculture. 20:123–134). However, natural isolates of *Phaffia rhodozyma* produce so little astaxanthin (typically 100 to 300 parts per million (ppm)) that they are not practical or economical pigment sources for aquaculture (Torrissen, Hardy and Shearer. 1989. Reviews in Aquatic Science 1:209–225, Johnson and An. 1991. CRC Crit. Rev. Biotech. 11:297–326). If Phaffia strains are to be an economically feasible feed additive for coloring aquatic animals, or any other potential foodstuff (animal or otherwise), then astaxanthin over-producing strains must be developed. Each of the references cited in this paragraph are incorporated herein by reference.

Mutants of naturally occurring "wild-type" Phaffia have been described in the literature, allegedly capable of generating higher levels of astaxanthin than the wild-type yeasts (International Publication No. WO 88/08025 International Application No. PCT/DK88/00068); EPO Publication No. 0 438 182 A1 (EPO Application No. 91900682.3); EPO Publication No. 0 454 024 A2 (EPO Application No. 91106436.8); International Publication No. WO 91/02060 (International Application No. PCT/US90/00558); EPO Publication No. 0 474 347 A1 (EPO Application No. 91306489.5); and EPO Publication No. 0 427 405 A1 (EPO Application No. 90311254.8), all of which are incorporated herein by reference). These strains reportedly produce higher levels of astaxanthin than the wild-type isolates under specific conditions. However, these mutant strains produce higher levels of astaxanthin only at relatively low biomass concentrations. At relatively high biomass concentrations, these mutant strains produce only low levels of astaxanthin which are not high enough to be practical.

Thus far, none of the reported Phaffia strains are capable of producing astaxanthin efficiently enough to compete economically with synthetic astaxanthin. Commercially viable strains have to produce astaxanthin at substantially higher levels than strains reported in the literature. To develop an economically viable astaxanthin production process, a strain should produce in excess of 3,000 ppm, preferably in excess of 4,000 ppm, astaxanthin based on dry yeast solids at more than 4 wt %, preferably more than 6 wt %, dry yeast solids (dys) in a large volume of nutrient medium, e.g. 1,500 liters (l) or more. As here used, "wt % dry yeast solids" or simply "dry yeast solids" are washed solids determined by the method described in Official Method of Analysis, A.O.A.C. 14th Edition (1984) Sections 10.215–10.225, which is incorporated herein by reference.

Besides the need to develop a suitable strain of *Phaffia rhodozyma* for commercial astaxanthin production, methods for cultivating *Phaffia rhodozyma* also need to be developed which maximize astaxanthin production in large fermentors. Only limited literature sources are available dealing with the growth of Phaffia and production processes of astaxanthin in large fermentors (International Publication No. WO 88/08025 (International Application No. PCT/DK88/00068), and EPO Publication No. 0 454 024 A2 (EPO Application No. 91106436.8) both of which are incorporated herein by reference). These reported fermentation processes give significantly lower yeast solids and astaxanthin levels than that required for an economically viable commercial scale fermentation process.

Not only do the various elements of producing astaxanthin from yeast cells require improvement, but so do the elements of astaxanthin absorption and deposition in animal flesh and animal products. Carotenoid absorption and deposition in fish are affected by various factors: genetics, size, age, sex, duration of pigment feeding, environmental factors, and diet composition (Torrissen, Hardy and Shearer: 1989: Reviews in Aquatic Science, 1:209–225, which is incorporated herein by reference).

Various reports are available concerning the formulation of Phaffia or carotenoid products (International Publication No. WO 88/08025 (International Application No. PCT/DK88/00068), EPO Publication No. 0 474 347 A1 (EPO Application No. 91306489.5), EPO Publication No. 0 454 024 A2 (EPO Application No. 911064368), and Japanese Patent Applications 57-206342, 2238855 and 90 JP-285090 are exemplary, all of which are incorporated herein by reference). In these reports, Phaffia products were formulated in order to protect the pigments during drying as well as during subsequent processing into fish feed. Various antioxidants and stabilizers were added to Phaffia preparations for those purposes.

The body temperature of salmonid fishes is equal to the temperature of the water in which they inhabit, e.g. generally 0 to 14 degrees Centigrade (C.). This means that the body temperature of these fishes can be, and occasionally is, lower than 10 C. Astaxanthin in Phaffia is concentrated in oil droplets. Phaffia oil contains about 13% palmitic acid (16:00) with a melting point of 64 C., and about 32% oleic acid (18:1n9) with a melting point of 16 C. Because of these high melting point fatty acids, Phaffia oil solidifies near 10 C. This makes it difficult for fishes to incorporate Phaffia astaxanthin at water temperatures below 10 C. at which Phaffia oil is solidified.

SUMMARY OF THE INVENTION

In one embodiment of the present invention, we have developed and isolated novel strains of *Phaffia rhodozyma* which produce greater than 3,000 ppm, often more than 4,000 ppm, astaxanthin based on dry yeast solids at more than 4 wt %, often more than 6 wt %, dry yeast solids when grown under suitable conditions and in a working volume of nutrient media of at least about 1,500 l. These Phaffia strains can produce astaxanthin economically on a commercial production scale for the aquacultural and food industries. Certain of these Phaffia strains were deposited with the American Type Culture Collection of Rockville, Md., on Apr. 6, 1993 under numbers ATCC-74218 (UBV-AX1), ATCC-74219 (UBV-AX2), ATCC-74220 (UBV-AX3), and ATCC-74221 (UBV-AX4).

In another embodiment of this invention, we have discovered methods for the cultivation of *Phaffia rhodozyma* cells which produce high yeast solids and high levels of astaxanthin. Generally, these methods include providing special fermentation conditions that promote the growth of the organism in terms of an increase in cell numbers during a growth phase, and in terms of an enhanced and steady accumulation of astaxanthin in the cells during a maturation phase. More specifically, these methods include exposing the yeast cells during the growth and maturation phases of fermentation to a source of light, and/or extending and stimulating the astaxanthin formation during the maturation phase by controlling the feed rate of fermentable sugar, e.g. glucose, or by providing the yeast cells with energy sources that are slowly metabolized, e.g. glycerol.

In another embodiment of this invention, we have discovered that the Phaffia strains of this invention need not be disrupted to make astaxanthin available to salmonids, sea bream, crustaceans, and other animals. Astaxanthin in undisrupted cells is more stable during drying, storage and feed preparation processes.

In yet another embodiment of this invention, we have discovered that a novel formulation of Phaffia product increases the astaxanthin deposition in fishes. This formulation is a blend of undisrupted Phaffia cells, vegetable oil or a blend of vegetable oils with a low solidification point, an emulsifier, and an antioxidant.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Mutagenesis

Figure 1:
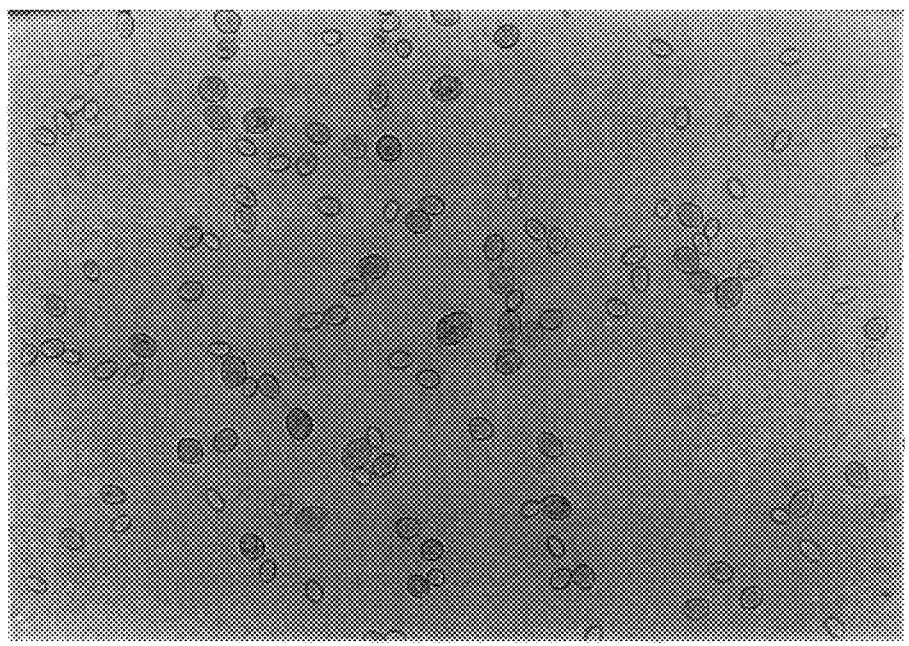
FIGS. 1–8 are photomicrographs showing the appearance of various mutant strains.

Astaxanthin over-producing yeast strains can be obtained by consecutive mutagenesis followed by suitable selection of mutant strains which demonstrate superior astaxanthin production. Preferably the yeast cells are of the genus Phaffia, and more preferably of the species *Phaffia rhodozyma*. Starting wild type yeast cell strains include those on deposit with the various culture collections throughout the world, e.g. the ATCC and the Centraalbureau voor Schimmelcultures (CBS). Typically it is necessary to perform two or more consecutive rounds of mutagenesis to obtain desirable mutant strains.

Any chemical or nonchemical (e.g. ultraviolet (UV)) radiation) agent capable of inducing genetic change to the yeast cell can be used as the mutagen. These agents can be used alone or in combination with one another, and the chemical agents can be used neat or with a solvent.

In those mutagenesis protocols employing a chemical mutagen, typically the mutagen is introduced into a buffered volume of cells, thoroughly mixed, and then the tubes are incubated at room temperature for 1 to 12 hours (hr) with continuous gentle agitation. After the incubation, the reaction mixture is plated directly onto agar medium plates. The composition of the agar can vary, but typically the composition includes glucose (or other carbon source), yeast extracts (such as those available from Universal Foods Corporation), agar, and a screening agent that inhibits pigment formation and/or cell growth. The cells are distributed evenly across the agar surface, usually by shaking with sterile 5 millimeter (mm) glass beads The plates are then inverted and incubated at about 21 C. for 6–10 days under illumination which is preferably a continuous low-intensity light. Similar growing techniques are employed for those mutagenesis protocols in which the mutagen is a nonchemical.

Screening for High Astaxanthin-Producing Mutants
Initial Screening on Plates and in Shake Flasks After the incubation period, those yeast colonies that appear better pigmented to the human eye than the mutagenized parent strain are collected and subcultured onto new agar plates (often of the same composition as those used to grow the mutagenized parent strain). After an additional incubation period of 6–10 days under like conditions, the new isolates that continue to be heavily pigmented are inoculated into flasks, e.g. 50 ml flasks containing 10 ml of a blend of glucose and yeast extract. The isolates are then typically incubated for another 6–10 days under similar conditions to the previous incubations but this time on a shaker operating at about 200 revolutions per minute (rpm). After this incubation period, an aliquot (e.g. 0.2 ml) is taken and the total carotenoid content and astaxanthin content determined. Those strains exhibiting enhanced astaxanthin producing capabilities are candidates for additional screening in a small batch fermentation, and are typically stored by freezing in an appropriate medium, e.g. 15 vol % glycerol at minus 80 C., until required for the next mutagenesis or screening. This storage technique can be used after any of the screening steps or for simply maintaining production strains.

Screening in a Small Batch Fermentation

Following selection of appropriate astaxanthin producing mutants at the 50 ml flask level, mutants are then usually screened for performance in 2 l fermentors (e.g. Omni-Culture Fermentors, Virtis Corp., Gardiner, N.Y.) containing approximately 1.5 l of nutrient medium. In a typical screening procedure at this level, 250 ml flasks containing 30 ml of a blend of glucose and yeast extract are each inoculated with 100–250 μl of mutant yeast cells taken from a frozen stock of the strain of yeast cells that is to be tested. These flasks are then shaken at 200 rpm at 20–22 C. under continuous light for 3 days. Aliquots of these cell cultures (15–20 ml) are then used to inoculate into the fermentors.

The working volume in these 2 l fermentors is usually 1.5 l of an enriched glucose yeast extract medium supplemented with various vitamins and minerals in assimilable form. Typical of these vitamins and minerals are ammonium sulfate, potassium phosphate, magnesium sulfate, zinc sulfate, ferric ammonium sulfate, copper sulfate, inositol, pyridoxine hydrochloride, thiamine, calcium pantothenate, biotin, and the like. The combinations and concentrations of these materials, including the glucose and yeast extracts, can vary to convenience. If desired, an antifoam agent and/or other additives can also be incorporated into or used with the medium.

The fermentor with its medium is sterilized by autoclaving. The pH of the media is usually maintained between 4.5 and 7, and the temperature between 15–24 C. The medium is usually sparged with filter sterilized air (e.g. 2 liters per minute (1/min)), and it is continuously agitated (e.g. 700 rpm). Fermentations typically last 4–6 days, and they are sampled periodically for cell growth and astaxanthin production. Strains showing appropriate levels of growth and astaxanthin production are candidates for screening at the fed-batch fermentation level.

Screening in a Fed-Batch Fermentation

Following identification of astaxanthin over-producing mutants in small batch fermentations, mutants are further screened for fast growth rate, high solids production and high astaxanthin production levels in 14 l, 20 l, 250 l and 2,000 l fermentors. Typically, strains are propagated in fermentors over a pH range of about 4.5 to 7 controlled with aqueous ammonia, sodium hydroxide or both at a temperature range of 15 to 24 C. Agitation and aeration are adjusted as necessary to maintain desired growth rates. The media with which the fermentors are charged are compositionally similar to those used in the small fermentors, i.e. they contain glucose (or other suitable carbon source) yeast extracts, vitamins minerals and other additives, all in assimilable form, although the exact recipe may and probably will vary from that used for the small fermentors. Antifoam agents and other processing aids can be used as desired.

The culture can be conducted as a batch fermentation until a desired cell density is obtained, or the glucose (or other suitable carbon source) supply can be started immediately. This supply is adjusted as necessary to obtain the best yeast growth rate and astaxanthin production. Additional nitrogen can be supplied to the fermentation in the form of ammonia or urea.

Cultivation of *Phaffia rhodozyma*

The Phaffia strains of this invention initially show rapid growth which gradually slows as they approach a high cell concentration, e.g. greater than 6 wt % biomass solids. In a typical fermentation, the rate of astaxanthin formation is initially slower than the growth rate of the Phaffia cells, but ultimately (during the later phase of the fermentation) the rate of astaxanthin formation exceeds the cell growth rate. We have termed this later phase the "maturation phase". We have found that the rate of astaxanthin production is highest during the early stages of the maturation phase.

In order to obtain better astaxanthin-producing fermentations, we have developed three approaches to sustain or enhance the high rate of astaxanthin production that occurs during the early stages of the maturation phase. During this enhanced maturation phase, the astaxanthin concentration is increased over the standard maturation phase by at least 2-fold, often 3-fold or more. The first technique is to expose the yeast cells to a light source, preferably a continuous, low-intensity light, during the maturation phase, particularly from its inception to that point in the phase at which the rate of astaxanthin production begins to significantly decline.

An and Johnson (Antonie van Leeuwenhoek. 1991. 57: 191–203, which is incorporated herein by reference) indicated that high intensity light inhibits the growth and carotenoid production by Phaffia. Evans, et al. (EPO Publication No. 0 427 405 A1, EPO Application No. 90311254.8) indicate that Phaffia strains do better in daylight than in darkness. Both studies used Phaffia grown on agar plates. Like An and Johnson, we found that continuous fluorescent light (regular lab lighting) reduced pigment yields of Phaffia in shake flasks, and like Evans we found darkness to be inhibitory of carotenoid development in some Phaffia strains. However, we also found that a low-intensity, preferably continuous, fluorescent light, i.e. less than about 100, preferably less than about 25 watts per kiloliter fermentation broth, actually promotes carotenoid production in some Phaffia strains grown in liquid media. These strains include those on deposit with the American Type Culture Collection bearing numbers ATCC-74218, ATCC-74219, ATCC-74220 and ATCC-74221. We have also found that better astaxanthin production is obtained when these strains are provided with such a source of light during fed-batch fermentation. The light is not limited to any particular wavelength, but light of 250 to 700 nm, particularly visible light, is preferred. In those circumstances in which the fermentor is constructed of metal or another opaque material, the light can be made available through one or more glass (or similarly translucent material) ports while the nutrient medium containing the yeast cells is continually circulated past the port(s). Fermentation broth can also be pumped in a return circuit through a light transparent tube and returned to the fermentor. In both these cases a high-intensity light, e.g. a light that delivers more than 15 w/kl can be used since only a relatively small surface area is exposed to the light.

Second, the yeast cells are provided with a controlled amount of a rapidly, relative to a polysaccharidee metabolized energy source, e.g. glucose or sucrose. During the growth phase, the yeast cells are fed this energy source, typically glucose, as rapidly as possible with the proviso that it does not accumulate in the nutrient medium to any substantial extent. This rate will vary with the yeast cell strain, the composition of the nutrient medium, the fermentation protocol, and similar factors. The accumulation of the energy source in the medium is generally a signal that the growth phase is ending and the maturation phase is beginning.

After the desired yeast solids is achieved and prior to the accumulation of the energy source, the feed rate of the energy source is reduced to at least about 50%, preferably at least about 40%, more preferably at least about 30%, of the maximum feed rate during the growth phase. During this period of reduced energy source feed, the yeast cells continue to produce astaxanthin, but the growth in the number of yeast cells, i.e. the growth in the cell density, is restricted. This period is allowed to continue until the cells no longer produce astaxanthin at an economically desirable rate.

To maximize the accumulation of astaxanthin during the maturation phase, the energy source feed rate can be reduced in a step-wise or continuous manner. For example, with the onset of the maturation phase, the energy source feed rate can be reduced by 50% and after a certain period of time, typically 12 to 24 hours, it can be reduced another 50%.

The third technique is to feed the yeast cells a slowly, relative to glucose, metabolized energy source during the growth and/or maturation phases. These energy sources or maturation extenders include most materials that can be slowly metabolized by a yeast cell. Glycerol; polymerized forms of glucose, sucrose, and other polysaccharides typically found in molasses and certain corn syrups; various alcohols such as methanol, ethanol, etc.; and various organic acids such as succinic, glutamic, maleic; etc, are exemplary of these extenders.

In one embodiment of this technique (and like the reduced energy source feeding technique), these extenders are fed to the yeast cells at the time energy source (e.g. glucose) accumulation is detected in the nutrient medium, and they are fed in an amount and in a manner such that the astaxanthin production of the cells continues at a desirable rate. As this astaxanthin production rate slows, the amount of extender fed to the cells is reduced accordingly. The exact amounts and the rate of extender fed will vary with the strain, fermentation protocol, and like considerations.

In another embodiment of this technique, these slowly metabolized extenders can be fed to the yeast cells during the growth phase as part of or in addition to the energy source feed. In this circumstance, the yeast cells will first deplete the rapidly metabolized energy source, e.g. glucose, and as their rate of consumption of this energy source slows, this signals that the growth phase is ending and the maturation phase is beginning. At this time, the addition of the energy source to the nutrient medium is stopped and as the remaining rapidly metabolized energy source in the medium is exhausted, the yeast cells will begin to metabolize the remaining slowly metabolized energy sources. These remaining slowly metabolized energy sources can be supplemented, as desired, with additional materials as described above.

The use of maturation extenders, in either format, will extend this period in a manner similar to the other two extension techniques. In addition, these techniques can be used in any combination with one another, and typically the continuous light technique is used in combination with one of the feed techniques.

The early stages of the maturation phase continues until the astaxanthin production rate slows (as measured in the production of astaxanthin per unit volume per unit time, e.g. mg/l/hr). This usually occurs 2 to 4 days after the end of the growth phase. The rate is, of course, a continuum and at some point after it begins to decrease from the maximum, the early stages of this phase are over and continuation of the maturation phase becomes economically undesirable and it is terminated.

Yeast Cell Recovery and Product Preparation

Phaffia yeast is manufactured as a pure culture fermentation product. Fermentation raw materials are selected from a number of vendors based on availability and suitability for the process. The major components for the growth of *Phaffia rhodozyma* include high dextrose equivalent (DE) corn syrup (or equivalent source of fermentable sugars), yeast extract, ammonia, inorganic phosphates, and magnesium sulfate. In addition to these major components, a number of micronutrients, such as trace metals and vitamins, are required. All of these nutrients are commonly used in commercial fermentation processes, including the manufacture of yeast for feed and food. Each component is optimized to generate the maximum yield of Phaffia yeast astaxanthin. Foaming during the fermentation is controlled through the addition of food approved defoaming agents.

The fermentation is conducted in pure culture fermentors which have been cleaned and sterilized prior to use. All nutrients added to the fermentors during the fermentation process are sterilized before use.

The production of Phaffia yeast described in this invention consists of a fed-batch fermentation. Other fermentation techniques can be used if desired. The addition of nutrients during the fermentation is optimized to achieve rapid production of both the Phaffia yeast biomass and astaxanthin.

During the fermentation a number of conditions are controlled and maintained. These include the acidity of the medium, the fermentation temperature, and the degree of aeration.

The fermentation is usually terminated when the astaxanthin production falls below a commercially desirable level, and it is terminated typically by transferring the culture (i.e. fermentation broth) from the fermentor by any conventional means to a refrigerated storage vessel to await concentration by centrifugation or filtration. Continuous centrifuges or filtration units are used for the preliminary concentration of the fermentation broth. The fermentation broth is passed through these units, and the yeast concentrate (i.e. yeast cream) is transferred to a refrigerated yeast cream storage tank.

An edible antioxidant, such as ethoxyquine vitamin E, butylated hydroxyanisole (BHA), butylated hydroxytoluene (BHT), or ascorbyl palmitate; an edible oil such as a vegetable oil, e.g. corn oil, safflower oil, sunflower oil, soybean oil, etc.; and an edible emulsifier, such as soy bean lecithin or sorbitan esters, can be added to the yeast cream at this stage. As here used, "edible" means a material that is approved for human or animal consumption. This serves to protect the astaxanthin during processing and shipment and also improves the pigment deposition in fish flesh.

The oil, emulsifier and antioxidant can be added at any convenient time during Phaffia yeast processing. In one embodiment, the oil, or blend of oils, emulsifier(s), and one or more antioxidants, are blended with one another, and then the blend is mixed with the broth concentrate (yeast cream), dried, and packaged for shipping. In another embodiment, the oil, emulsifier and antioxidant are added to the yeast cream after it has been dried. In yet another embodiment, one or two of the additives are blended with the yeast cream prior to drying, while the remaining additive(s) are blended with the yeast cream after it has been dried. The oil or blend of oils comprises between about 0.1 and 10 wt % the emulsifier(s) between about 0.1 and 10 wt %, and the antioxidant between about 0.02 and 2 wt % based on the total weight of the final dry product.

Prior to drying, the cream is standardized to a suitable astaxanthin content usually 3,000, 4,000 or 5,000 milligrams per kilogram of the product (mg/kg) through the addition of feed yeast (Yeaco™-20 produced by Universal Foods Corporation or equivalent).

The standardized product is then dried by any suitable means, e.g. spray drying, drum drying, etc., and eventually packaged, typically in either 20 or 25 kg, heat-sealed, polylined boxes. The packaging is designed to protect the product from light, oxygen, and moisture.

In one embodiment of this invention, the yeast cream is dried using conventional equipment and techniques, such that a substantial number, preferably a substantial majority, of the cells are not disrupted by the process, i.e. such that the cells retain the bulk of their spherical shape. We have found that unbroken yeast cells provide astaxanthin to consuming animals as, or nearly as, efficiently as broken cells.

In another embodiment of this invention, the yeast cream is dried in a manner that promotes disruption of the cells such that most of the cells in the dried product are broken or fragmented, i.e. the cells no longer retain their substantially spherical shape. If such broken cells are desired and not provided by the drying process then the cells can be subjected to a milling step or enzymatic treatment in which the cells are broken.

The following examples are illustrative of certain specific embodiments of this invention. Unless indicated to the contrary all parts and percentages are by weight.

SPECIFIC EMBODIMENTS

Pigment Extraction and Astaxanthin Analysis

Astaxanthin content is determined as reported by Sedmak, Weerasingh, and Jolly in Jolly. 1990. Biotechnol. Techniques 4:107–112, which is incorporated herein by reference.

Yeast cells are washed twice in 12×100 mm test tubes with 4 ml of deionized water. After washing and decanting the water, the test tubes containing the washed cell pellets are inverted to drain the water. The insides of the tubes are then wiped with tissue paper to remove most of the water from the tube. To each tube is then added 0.5 ml of dimethyl sulfoxide (DMSO) (Sigma Chemical Co, St. Louis, Mo.) preheated to 55 C. The tubes-are vortex agitated for 20–30 seconds (sec) and 0.1 ml of 0.02 M sodium phosphate (pH 7.0) then is added to partition the carotenoids into 1 ml of subsequently added organic solvent. For compatibility with high performance liquid chromatography (HPLC) analysis of astaxanthin, 1 ml of hexanes:ethyl acetate (50:50 volume basis, HPLC grade) is used. The tubes are then vortex agitated for 30–40 sec to mix the aqueous and organic phases. The phases are then separated by centrifugation for 3 min in a desk-top clinical centrifuge. The organic phase is removed and the pigmented carotenoid content of the organic phase determined from the absorbency at 480 nm ($A_{480}$). The total carotenoids are calculated using the extinction coefficient $E_{1\ cm}^{1\%}=2.150$ (based on determinations using authentic synthetic astaxanthin).

The astaxanthin content is then determined by HPLC. Samples for HPLC analysis are diluted in hexanes:ethyl acetate (50:50 volume basis), and then made to 0.1% acetic acid with glacial acetic acid and filtered prior to injection. The column is an Alltech (Deerfield, Ill.) Nucleosil 100 silica 5 micron, 250×4.6 mm stainless steel column with an Alltech guard column. The eluting solvent is hexanes:ethyl acetate (50:50 volume basis) without glacial acetic acid. The eluant is monitored at 476 nm. The percent astaxanthin is then calculated from the area under the curve at the position of a synthetic astaxanthin standard.

Astaxanthin concentration is then calculated as follows:

Total carotenoid in μg/ml of fermentation broth=($A_{480}/2,150$)× $10^4$×dilution factor Astaxanthin in μg/ml of fermentation broth=(Total carotenoid in μg/ml of fermentation broth×% Astaxanthin determined by HPLC)÷100

Astaxanthin in μg/g of yeast=Astaxanthin in μg/ml of fermentation broth÷g Dry yeast solids/ml

EXAMPLE 1

Development of Mutant Strains

*Phaffia rhodozyma* mutants ATCC-74218 (UBV-AX1), ATCC-74219 (UBV-AX2), ATCC-74220 (UBV-AX3) and ATCC-74221 (UBV-AX4) were developed from wild type strains by repeated mutagenesis as described in the section entitled Mutagenesis.

EXAMPLE 2

Cultivation of Novel Strains

The data in Tables 1, 2 and 3 demonstrate that the Phaffia strains of this invention grow to high levels of cell solids and produce high levels of astaxanthin in working volumes of various sizes. In some of the literature, astaxanthin is not distinguished from total carotenoids, and thus the actual level of astaxanthin is considerably lower than that reported. The astaxanthin values in the Tables below are based on HPLC quantifications of astaxanthin.

14 l Fermentation

About 30 g (dys basis) of actively growing culture in 15 l of appropriate growth medium are inoculated into a 14 l Virticulture fermentor (Virtis Corporation, Gardiner, N.Y.). A typical formulation for the set broth is:

| INGREDIENT | AMOUNT (g) |
|---|---|
| YEAST EXTRACT | 75 |
| AMMONIUM SULFATE | 25 |
| MONOBASIC POTASSIUM PHOSPHATE | 15 |
| MAGNESIUM SULFATE | 5 |
| INOSITOL | 0.65 |
| PYRIDOXINE | 0.35 |
| ZINC SULFATE | 0.15 |
| THIAMINE HYDROCHLORIDE | 0.1 |
| CALCIUM PANTOTHENATE | 0.08 |
| FERRIC AMMONIUM SULFATE | 0.05 |
| CUPRIC SULFATE | 0.01 |
| BIOTIN | 0.0005 |
| TAP WATER | 5 l |
| ANTIFOAM | 5 ml |
| pH | 5.5 |

Start-up conditions are 8 standard liters per minute (SLPM) aeration and 500 rpm agitation. The pH is controlled at 5.5 with 750 ml 1:3 dilution of reagent grade ammonium hydroxide, $NH_4OH$. Food grade antifoam is added as required The culture is fed 1750 g glucose (Cerelose™, CPC International, Summit-Argo, Ill.) as a 50% by weight solution at a rate such that the glucose concentration is less than 5 grams per liter (g/l) preferably between 0.1 and 2.5 g/l throughout the fermentation. Dissolved oxygen is controlled by agitation and airflow to between 20% and 90% saturation. Results of such fermentations with UBV-AX3 and 4 are presented in Table 1:

TABLE 1

Astaxanthin Production in 14 l Fermentor

| Strain | Time (hrs) | Solids (%) | Astaxanthin (µg/g dys*) |
|---|---|---|---|
| UBV-AX3 | 115 | 8.6 | 6660 |
| UBV-AX4 | 115 | 7.7 | 4670 |

*dys: Dry Yeast Solids 2000 l Fermentation

About 3.6 kg (dys basis) of actively growing culture in 120 l of appropriate growth media are inoculated into a 2000 l IF2000 New Brunswick Scientific fermentor (New Brunswick Scientific Corporation, Edison, N.J.) containing about 700 l of the broth described below.

| INGREDIENT | AMOUNT |
|---|---|
| YEAST EXTRACT | 6 kg |
| MONOBASIC POTASSIUM PHOSPHATE | 4 kg |
| MAGNESIUM SULFATE | 4 kg |
| DEXTROSE | 3 kg |
| SODIUM CHLORIDE | 700 g |
| FERROUS SULFATE | 55 g |
| CALCIUM PANTOTHENATE | 25 g |
| ZINC SULFATE | 15 g |
| CITRIC ACID | 5 g |
| MANGANOUS SULFATE | 3 g |
| COPPER SULFATE | 1 g |
| BIOTIN | 400 mg |
| COBALT SULFATE | 300 mg |
| THIAMINE HYDROCHLORIDE | 200 mg |
| BORIC ACID | 80 mg |
| TAP WATER | 700 l |
| ANTIFOAM | 200 ml |
| pH | 5.5 |

Start-up conditions are 700 SLPM aeration and 100 rpm agitations. The pH is controlled at 5.5 with anhydrous ammonia. Food grade antifoam is added as required. The culture is fed 800 kg of a 45% by weight solution of unrefined high dextrose corn syrup (Cargill Incorporated, Eddyville, Iowa) at a rate such that glucose does not accumulate in the fermentation broth to more than 5 g/l, preferably to 0.1–2.5 g/l. Dissolved oxygen is controlled by agitation and airflow to between 20% and 70% saturation. The volume of the broth upon termination of the fermentation is approximately 1,500 l. The results of such a fermentation with UBV-AX2 are presented in Table 2.

TABLE 2

Astaxanthin Production in 2,000 l Fermentor

| Strain | Time (hrs) | Solids (%) | Astaxanthin (µg/g dys*) |
|---|---|---|---|
| UBV-AX2 | 136 | 10.9 | 5321 |

*Dry Yeast Solids 40,000 l Fermentation

About 160 kg (dys basis) of actively growing culture in 4,000 l of appropriate growth media are inoculated into a 40,000 l fermentor. A typical formulation for the set broth is:

| INGREDIENT | AMOUNT (kg) |
|---|---|
| YEAST EXTRACT | 81 |
| MONOBASIC POTASSIUM PHOSPHATE | 68 |
| MONOBASIC SODIUM PHOSPHATE | 14 |
| MAGNESIUM SULFATE | 80 |
| DEXTROSE | 50 |
| FERROUS SULFATE | 0.650 |
| CALCIUM PANTOTHENATE | 0.470 |
| ZINC SULFATE | 0.150 |
| CITRIC ACID | 0.060 |
| MANGANOUS SULFATE | 0.035 |
| COPPER SULFATE | 0.035 |
| SODIUM MOLYBDATE | 0.020 |
| BIOTIN | 0.0035 |
| COBALT SULFATE | 0.0035 |
| THIAMINE HYDROCHLORIDE | 0.0018 |
| BORIC ACID | 0.0023 |
| TAP WATER | 13,500 |
| ANTIFOAM | 4 l |
| pH | 5.5 |

Start-up conditions are 8,000 SLPH aeration and 40 rpm agitation. The pH is controlled at 5.5 with anhydrous ammonia. Food grade antifoam is added as required. The culture is fed 17,000 kg of a 42% by weight solution of unrefined high dextrose corn syrup (Cargill Incorporated, Eddyville, Iowa) at a rate such that glucose does not accumulate in the fermentation broth to more than 5 g/l, preferably to 0.1–2.5 g/l. Dissolved oxygen is controlled by agitation and airflow between 20% and 70% saturation. Results of such a fermentation with UBV-AX1 are presented in Table 3:

TABLE 3

Astaxanthin Production in 40,000 l Fermentor

| Strain | Time (hrs) | Solids (%) | Astaxanthin (μg/g dys*) |
|---|---|---|---|
| UBV-AX1 | 157 | 7.8 | 5060 |

*Dry Yeast Solids

EXAMPLE 3

Strain Descriptions: Colony Morphology

Colony morphology of the novel strains were observed on 2–4 week old streak plates which contained 2% glucose, 0.5% Tastone™-154 (Universal Foods Co. Yeast Extract) and 1.5% agar.

UBV-AX1: Well isolated colonies are 4–5 mm in diameter. Some colony size heterogeneity exists within the culture. Smaller colonies range in size from 1–3 mm. Some of these smaller colonies can be darker in color than the rest of the colony population. Colonies edges are entire; but some colonies will show irregular edges. This becomes typical after 3–4 weeks. Colonies are convex to slightly umbonate. Color is red orange, darker at the raised center. Colony finish is matt. Where crowded some colonies appear wrinkled, especially on older plates. After 3–4 weeks colony color is dark red. Lighter colonies, yellow to orange, can be occasionally seen in lawns of cells. These lawns can have a grainy appearance.

UBV-AX2: Well isolated colonies are 4–5 mm in diameter. Some colony size heterogeneity is present, with smaller colonies occasionally seen. Colony edges are entire. Colonies are convex to slightly umbonate and glossy in appearance. Color is red-orange, darker at the raised centers, especially where crowded. Occasional irregularities can be seen at some colony edges. After 3–4 weeks colonies are still glossy and dark red. Lawns of cells remain smooth and glossy. The lack of lighter colored colonies indicates that the genes for pigmentation in this strain are very stable.

UBV-AX3: Colony morphology can be heterogeneous, especially after 6 days growth in glucose/yeast extract broth. After 10 days on glucose/yeast extract plates, the colonies range in size from 1.5 to 3 mm in diameter. Color ranges from red to orange. Smaller colonies are typically darker red than the larger colonies.

UBV-AX4: After two weeks on glucose/yeast extract plates, colonies are 2–3 mm in diameter. The colony edges are entire, although a small number of colonies may show scalloped edges. Colony color is a dark red-orange. The colonies are glossy, and have a conical profile, especially where crowded. After 3 weeks, the colony profile shows flattening at the base. The color of the colony center is darker red than the perimeter. Colony edges remain entire.

EXAMPLE 4

Strain Description: Microscopic Appearance

Microscopic appearance of cells were observed on the novel strains grown in 2% glucose, 0.5% Tastone™-154 for 6 days.

Figure 2:
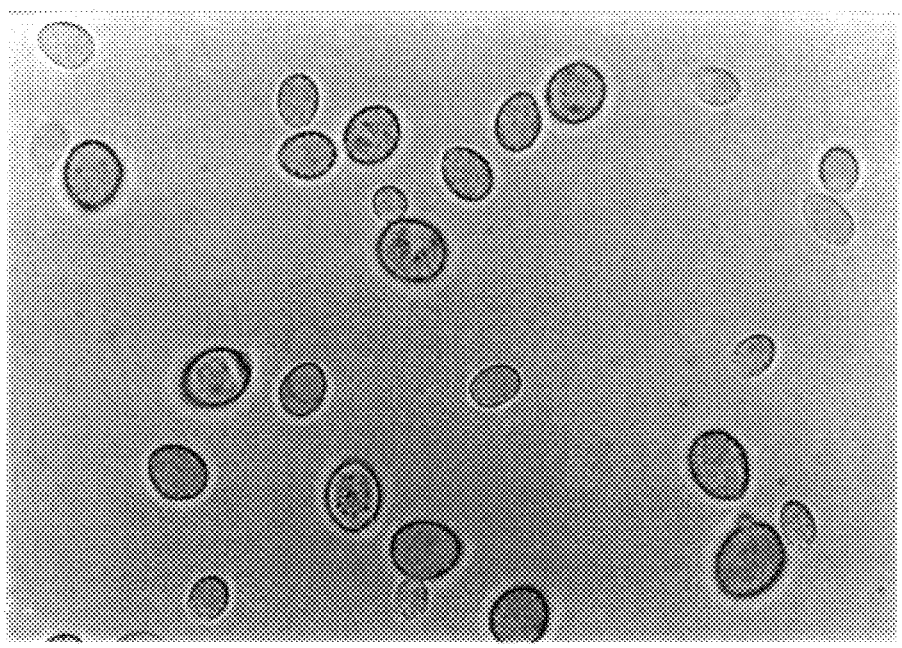

UBV-AX1 (FIGS. 1 and 2): Cells are single or in pairs with occasional short chains. Cells are ellipsoid to oviform Cells are reddish-tan. Some cells are devoid of cytoplasm with lipid droplets. Cells with granular, slightly pigmented forms are seen. Some pleomorphic shapes are also seen. Occasional apiculate shaped cells are present.

Figure 3:
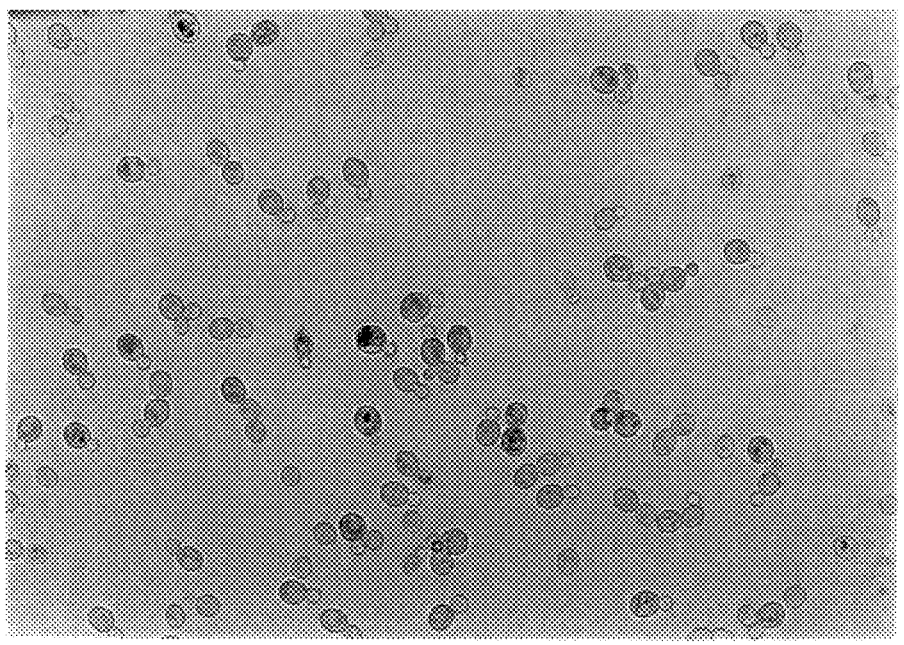
Figure 4:
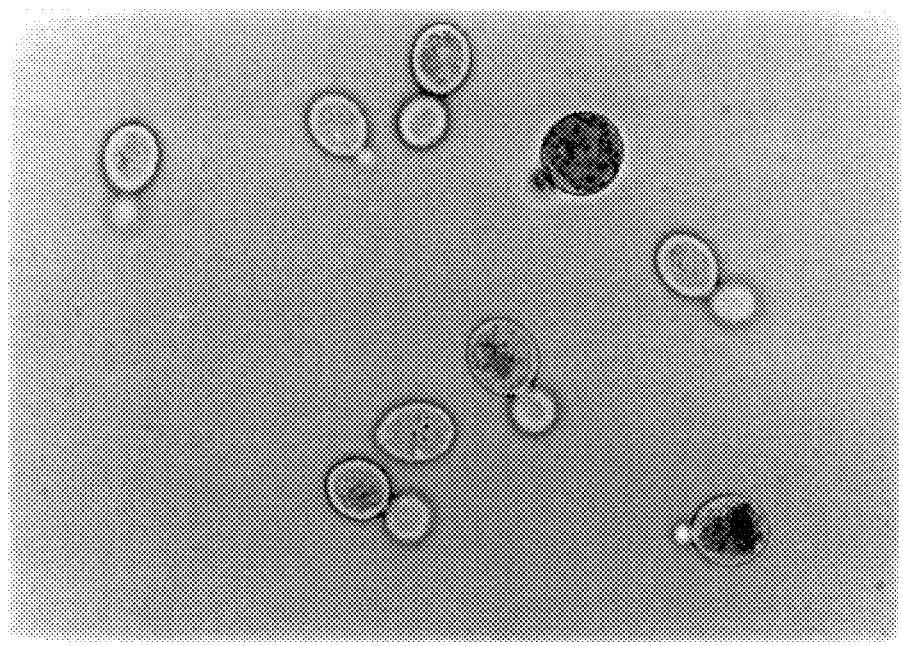

UBV-AX2 (FIGS. 3 and 4): Cells are single or in pairs. Cells with two buds at the same end of a mother cell are common. Cells are oblate ellipsoidal to globose. Many cells are obviously pigmented reddish brown. Cells with granular appearing, pigmented cytoplasm are fairly common. Occasional enlarged, deeply pigmented, rounded "chlamydospore-like" structures are seen. The structures lack the thickened cell walls of chlamydospores.

Figure 5:
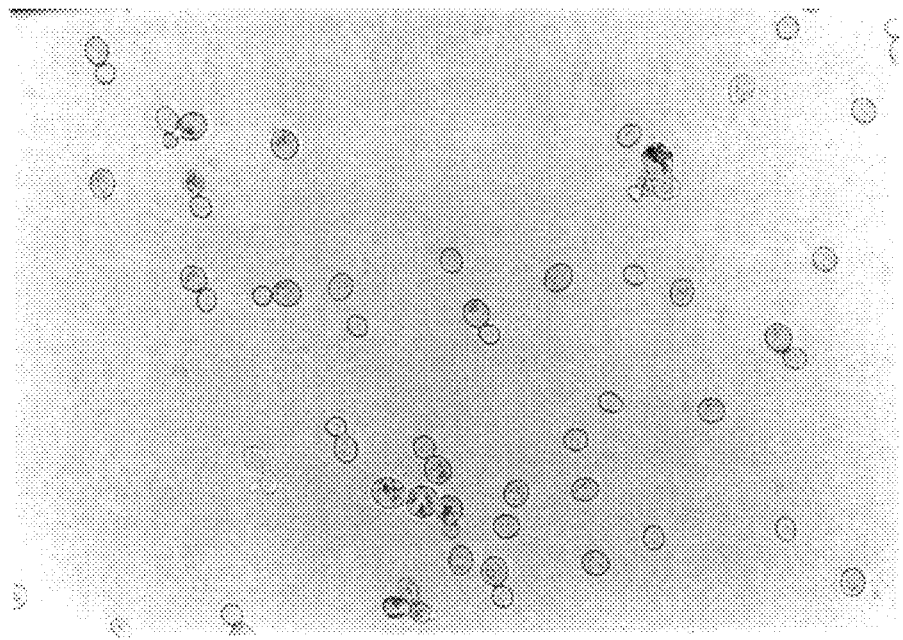
Figure 6:
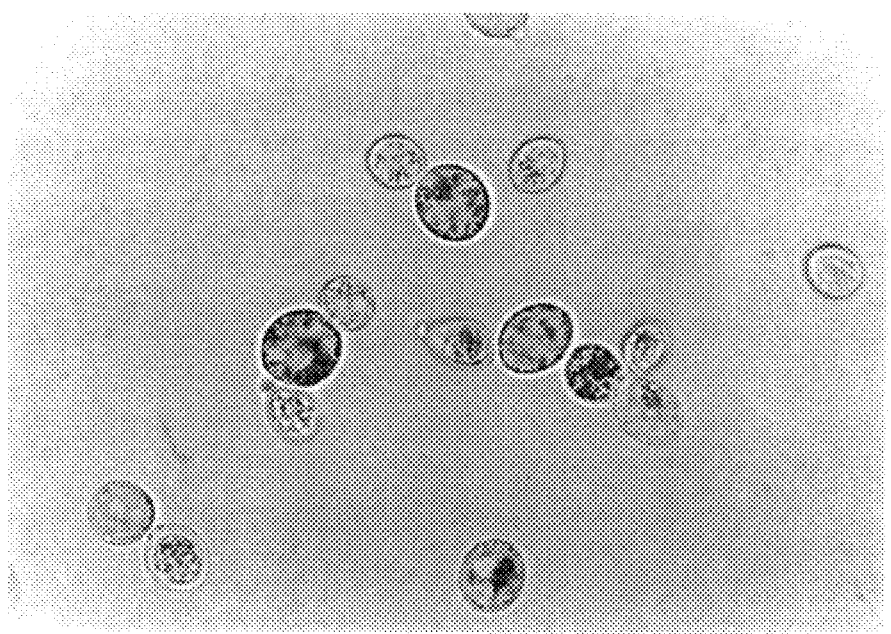

UBV-AX3 (FIGS. 5 and 6): Cells are single, in pairs, short chains or small clumps of 3 to 6 cells. Pleomorphic forms are seen. Many cells are obviously pigmented. The cytoplasm in these cells appear granular.

Figure 7:
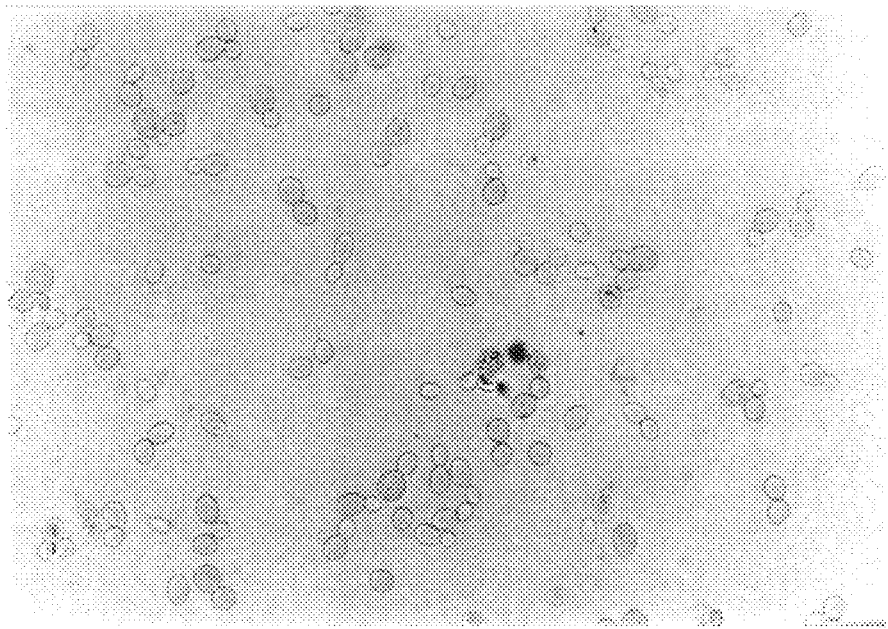
Figure 8:
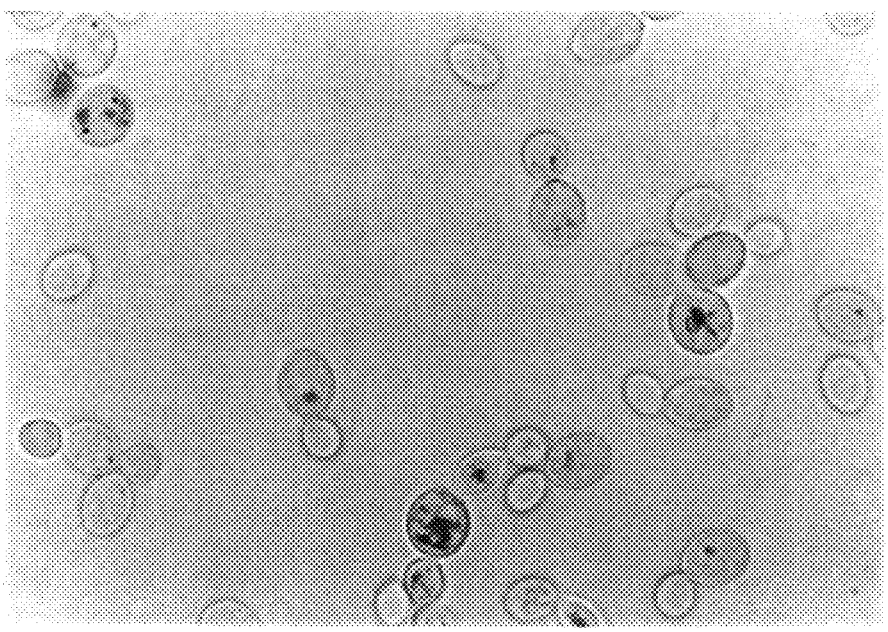

UBV-AX4 (FIGS. 7 and 8): Cells are single or in pairs or short chains. Pleomorphic forms are seen. Some cells have reddish-brown granular cytoplasm. Some cells appear to have red-crystalline structures present. Lipid droplets are very obvious in some cells.

EXAMPLE 5

Strain Description: Cell Sizes

Table 4 shows cell sizes of the novel strains which were grown in 2% glucose and 0.5% Tastone™-154 for 6 days.

TABLE 4

Cell Sizes of Certain Phaffia Strains

| Strain | Cell Size Range (μm) |
|---|---|
| UBV-AX1 | 4.2 × 6.3 to 8.4 × 12.6 |
| UBV-AX2 | 4.2 × 5.3 to 9.5 × 10.5 |
| UBV-AX3 | 4.2 × 6.3 to 9.4 × 11.5 |
| UBV-AX4 | 4.2 × 5.2 to 9.4 × 10.4 |

EXAMPLE 6

Enhancement of Astaxanthin Production by Exposure to Low Intensity Light

Table 5 reports that darkness is inhibitory to pigment production in shake flasks. Phaffia was grown in shake flasks with 2% glucose and 0.5% yeast extract at 200 rpm at 21 C. for six days.

TABLE 5

Enhancement of Astaxanthin Production by Exposure to Low Intensity Light

| | Astaxanthin (μg/ml culture broth) | |
|---|---|---|
| Strain | Continuous 10 ft-C Light | Dark |
| UBV-AX1 | 30.1 | 19.2 |
| UBV-AX2 | 43.8 | 17.3 |
| UBV-AX3 | 41.6 | 16.1 |

EXAMPLE 7

Hydrolyzed Corn Syrup

Hydrolysed corn syrup (DE=95) and a partly hydrolysed corn syrup (DE=63) are mixed to produce a feed material which contains glucose and significant levels of various higher sugars such as maltose, maltotriose and higher polymerized sugars. These sugars or polysaccharides are not metabolized until the glucose is depleted. A 75:25 mixture of these two corn syrups produces a feed of about 78% glucose and 10% maltose (about DE=87).

The data in Table 6 shows that UBV-AX1 produces significantly higher levels of astaxanthin in a 20 l fermentor with a 75:25 mixture of a hydrolysed corn syrup (DE=95) and a partly hydrolysed corn syrup (DE=63) than with a hydrolyzed corn syrup (DE=95) alone.

TABLE 6

Astaxanthin Production Levels
with DE = 87 and DE = 95 Corn Syrup

| Feed Corn Syrup | Yeast Solids % | Astaxanthin ($\mu$g/g dys*) |
|---|---|---|
| DE = 87 | 5.9 | 6,712 |
| DE = 95 | 5.9 | 5,892 |

*Dry Yeast Solids

EXAMPLE 8

Glycerol Effect on Astaxanthin Production During Maturation

For most Phaffia strains astaxanthin synthesis continues after growth has stopped. Astaxanthin is therefore considered by some to be a secondary metabolite in Phaffia. We have found that the addition of glycerol to Phaffia stimulates carotenoid synthesis during the non-growth phase after the primary carbon source (glucose) has been utilized. HPLC analysis indicates that if glucose and glycerol are present together, the glucose is preferentially utilized and the glycerol is used only after glucose depletion. As seen in the following tables, inclusion of glycerol along with glucose greatly enhances the astaxanthin yield of our Phaffia strains. These strains grow very poorly if glycerol is the only carbon source.

Table 7 shows that the astaxanthin production level of *Phaffia rhodozyma* is greatly increased by glycerol in shake flasks with 2% glucose and 0.5% yeast extract in continuous low intensity light for six days.

TABLE 7

Glycerol Effect on Astaxanthin Production
in Shake Flasks

| | Astaxanthin ($\mu$g/ml culture broth) | |
|---|---|---|
| Strain | Without Glycerol | With 1% Glycerol |
| UBV-AX1 | 30.0 | 37.6 |
| UBV-AX2 | 42.8 | 49.2 |
| UBV-AX3 | 54.2 | 71.3 |
| UBV-AX4 | 42.0 | 56.7 |

EXAMPLE 9

Slow Feeding During Maturation

The data of Table 8 shows the effect on maturation with and without a continued feed of the energy source. Fermentations were conducted in 20 l Chemap fermentors with UBV-AX1 and the standard fermentation format substantially as described above. In Case 1 the fermentation was ended as the growth rate of cells declined. In Case 2, feeding of the energy source was terminated as cell growth rate declined and the cells were allowed to mature for 72 hours. In Case 3, the feed rate of the energy source was reduced to 25% of the maximum feed rate as the yeast growth rate declined and the cells were allowed to mature for 72 hours with slow feeding.

TABLE 8

The Effect of Slow Feed During Maturation Phase
on Astaxanthin Production Levels

| Case | Feed during Maturation | Yeast Solids % | Astaxanthin ($\mu$g/ml fermentation broth) |
|---|---|---|---|
| 1 | No maturation | 7.0 | 175 |
| 2 | Maturation without feed | 5.9 | 362 |
| 3 | Maturation with slow feed | 7.9 | 561 |

EXAMPLE 10

Evaluation of the Novel Strains as a Source of Pigment for Salmonids

This example demonstrates that the novel strains of *Phaffia rhodozyma* pigment salmonids flesh effectively when supplied in feed as an additive. This example also shows that the strains of this invention do not require disruption to make astaxanthin available to salmonids (Binkowsky, Sedmak and Jolly. 1993. Aquaculture Magaine. March/April:54–59, which is incorporated herein by reference).

The Phaffia strain was grown in a 2,000 l fermentor in a manner substantially described as above. Cells were concentrated to 15–22% solids by centrifugation and dried. The feed was processed by Zeigler Bros. Inc., Gardners, Pa. The novel *Phaffia rhodozyma* or synthetic astaxanthin (5% Carophyll Pink, Hoffmann-LaRoche) were incorporated into their #1/8 Trout Grower pelleted food.

Rainbow trout (*Onchorhynchus mykisse*, Shasta strain) were obtained from a local commercial trout grower. After acclimation to laboratory conditions and an experimental control diet, the trout were moved into separate experimental tanks (28 fish per tank). The experimental tanks held approximately 250 liters of water (76 centimeter (cm) diameter; 56 cm standpipe) and had an average flow rate of 6.5 liters of water per minute.

Collectively, the procedures and diets employed in the experiments were designed to result in near-optimal growth of trout at 10 C., the approximate temperature at which most commercially-produced trout are raised. By the end of the experiment, the remaining trout were approximately market size.

At 4, 8 and 12 weeks, 6 fish per tank were randomly removed to determine growth rates and pigment levels. The fish were stunned by a blow to the head; total length measured; weight after blotting dry determined; and then each fish was cut across the isthmus severing the ventral aorta. The fish were allowed to bleed out in cool water and then two skin-on fillets were taken from each fish. With the information acquired from each sampling, tank biomass was recalculated and food rations adjusted so that each tank received 1.5% of its estimated biomass in food per day.

The fillets were processed to determine carotenoid content per wet weight of flesh. About 15 g of flesh pooled from various portions of a fillet were homogenized and 0.2 g samples of homogenized flesh extracted with 1 ml of acetone for 30 minutes at room temperature to release the flesh carotenoids. The carotenoids were then partitioned into hexanes:ethyl acetate (1:1 by volume) and the total carotenoid and astaxanthin content were determined as described above in the section entitled PIGMENT EXTRACTION AND ASTAXANTHIN ANALYSIS.

Pellets of food were crushed with a mortar and pestle. An accurately weighed portion (0.05 g) of the crushed pellets were treated with dimethylsulfoxide (DMSO) for 30 minutes at room temperature to extract the carotenoids. The DMSO extracted carotenoids were then quantified as described above in the section entitled PIGMENT EXTRACTION AND ASTAXANTHIN ANALYSIS. This procedure was used for feed analysis throughout the experimental trials.

The growth and pigmentation of rainbow trout that were fed diets containing our novel Phaffia yeast (one whole cells, the other milled or disrupted cells) were compared both to rainbow trout fed an unpigmented diet and to rainbow trout fed a diet containing synthetic astaxanthin.

Figure 9:
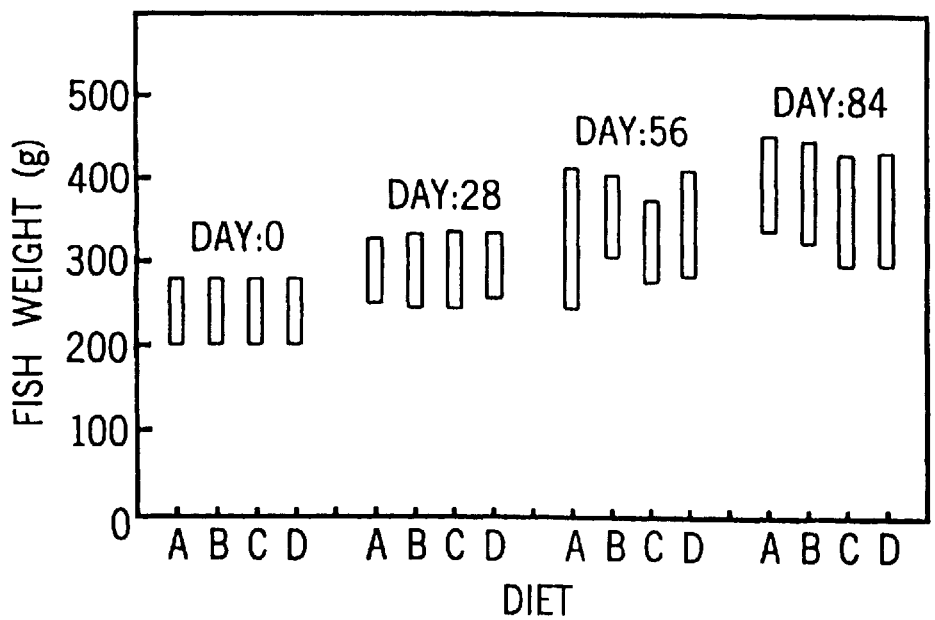
FIG. 9 describes the weight gain of rainbow trout over the course of a feeding trial.

As seen in FIG. 9, the weight gain of all four groups of fish was comparable with fish growing from approximately 240 g to 380 g during the 84 day trial period. This study indicates that whole or disrupted Phaffia yeast added to the diet at the above level gives the same or better palatability and digestibility as the control fish food. Gross anatomical examination of fish at 84 days indicated that there were no differences between the four treatment groups.

Figure 10:
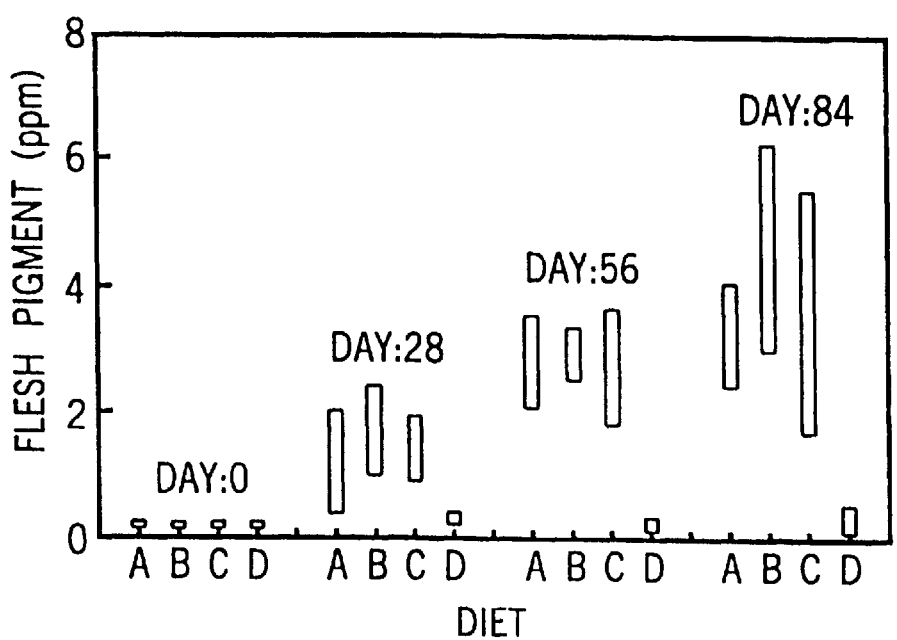
FIG. 10 describes the pigmentation of rainbow trout over the course of the same feeding trial as that of FIG. 9.

The flesh carotenoid content of rainbow trout fed the diet devoid of astaxanthin (Diet D) was the same low level at 0 and 84 days of feeding indicating that the base diet for these studies was indeed devoid of any carotenoid that might be deposited in the fish flesh. After 84 days of feeding, the flesh carotenoid content of the Phaffia and synthetic astaxanthin fed fish were the same (FIG. 10). All four groups of fish colored at comparable rates during the 84 day trial period.

EXAMPLE 11

Evaluation of a Novel Formulation of Phaffia Product for Pigmenting Salmonids This example demonstrates that a formulation of Phaffia cells blended with ethoxyquin, lecithin and safflower oil increases astaxanthin deposition in salmonid fish flesh.

Phaffia was grown in a 2,000 l fermentor in a manner as substantially described above. Cells were concentrated to 15–22% solids by centrifugation and dried. Ethoxyquin, lecithin and safflower oil were added to the yeast cream prior to drying The feed was processed by Zeigler Bros. Inc., Gardners, Pa. The treated and untreated Phaffia were incorporated into their #1/8 Trout Grower pelleted food.

Rainbow trout (*Onchorhynchus mykiss*, Shasta strain) were obtained from a local commercial trout grower. After acclimation to laboratory conditions and an experimental control diet, the trout were moved into separate experimental tanks (14 fish per tank) The experimental tanks held approximately 650 l of water (120 cm diameter; 56 cm standpipe) and had an average flow rate of 11 liters of water per minute.

Collectively, the procedures and diets employed in the experiments were designed to result in near-optimal growth of trout at 10 to 12 C., the approximate temperature at which most commercially-produced trout are raised. By the end of the experiment, the trout had grown from an average 300 g to an average 650 g. Fifteen fish were randomly sampled to determine base line weight, length and flesh color data before separating fish into experimental tanks. At 63 days 10 fish per tank and at 93 days 14 fish per tank were randomly removed to determine growth rates and pigment levels in the same manner as that described in Example 10. Similarly, the procedures of Example 10 were used to process the fillets (to determine carotenoid content per wet weight of flesh), and the pellets of food.

The growth and pigmentation of rainbow trout fed diets containing Phaffia yeast with and without lecithin and safflower oil were compared. Diet A contained Phaffia treated with 2,000 ppm ethoxyquin. Diet B contained Phaffia treated with 2,000 ppm ethoxyquin and 2.5% soy lecithin. Diet C contained Phaffia treated with 2,000 ppm ethoxyquin, 2.5% soy lecithin and 25% safflower oil.

TABLE 9

| Pigmentation of Fish Flesh at 93 Days | | |
|---|---|---|
| Diet | Astaxanthin in Feed (ppm) | in Flesh (ppm/wet wt) |
| A | 49 | 2.01 ± 1.32 |
| B | 49 | 3.02 ± 1.87 |
| C | 48 | 4.50 ± 1.40 |

As seen from the data in Table 9, after 93 days of feeding, fish fed the diet containing Phaffia treated with ethoxyquin, soy lecithin and safflower oil were pigmented best.

Although the invention has been described in considerable detail through the preceding examples, such detail is for the purpose of illustration. Many variations and modifications can be made by one skilled in the art without departing from the spirit and scope of the invention as described in the appended claims.

What is claimed is:

1. A method for the production of astaxanthin comprising: cultivating a *Phaffia rhodozyma* strain having all of the characteristics of ATCC-74281, ATCC-74219, ATCC-74220, ATCC-74221 and mutants thereof that retain astaxanthin-producing capability, wherein at last 3,000 ppm astaxanthin based on dry yeast solids is produced when cultivated under suitable conditions in a volume of nutrient medium of at least about 1500 liters and containing in excess of 4 weight percent yeast solids.

2. The method according to claim 1, wherein at least 4,000 ppm astaxanthin based on dry yeast solids is produced.

3. The method according to claim 1, wherein said volume of nutrient medium contains in excess of 6 weight percent yeast solids.

4. The method according to any one of claims 1–3, wherein the strain is ATCC-74218.

5. The method according to any one of claims 1–3, wherein the strain is ATCC-74219.

6. The method according to any one of claims 1–3, wherein the strain is ATCC-74220.

7. The method according to any one of claims 1–3, wherein the strain is ATCC-74221.

* * * * *

UNITED STATES PATENT AND TRADEMARK OFFICE
CERTIFICATE OF CORRECTION

PATENT NO. : 5,922,560

DATED : July 13, 1999

INVENTORS : Jacobson *et al.*

It is certified that an error appears in the above-identified patent and that said Letters Patent is hereby corrected as shown below.

In column 18, Claim 1, line 43, please delete "ATCC-74281" and insert therein --ATCC-74218--.

Signed and Sealed this

Seventh Day of December, 1999

*Attest:*

Q. TODD DICKINSON

*Attesting Officer*  Acting Commissioner of Patents and Trademarks